(12) United States Patent
Colosimo et al.

(10) Patent No.: US 10,161,893 B2
(45) Date of Patent: Dec. 25, 2018

(54) CHARACTERIZATION OF MATERIAL UNDER TEST (MUT) WITH ELECTROMAGNETIC IMPEDANCE SPECTROSCOPY

(71) Applicant: TransTech Systems, Inc., Schenectady, NY (US)

(72) Inventors: Donald D. Colosimo, Saratoga Springs, NY (US); Sarah E. Pluta, Scotia, NY (US); John W. Hewitt, Niskayuna, NY (US)

(73) Assignee: TransTech Systems, Inc., Latham, NY (US)

( * ) Notice: Subject to any disclaimer, the term of this patent is extended or adjusted under 35 U.S.C. 154(b) by 684 days.

(21) Appl. No.: 14/825,542

(22) Filed: Aug. 13, 2015

(65) Prior Publication Data

US 2016/0054247 A1 Feb. 25, 2016

Related U.S. Application Data

(60) Provisional application No. 62/039,204, filed on Aug. 19, 2014.

(51) Int. Cl.
*G01N 27/02* (2006.01)
*G01N 33/38* (2006.01)

(52) U.S. Cl.
CPC ......... *G01N 27/026* (2013.01); *G01N 33/383* (2013.01)

(58) Field of Classification Search
CPC ........................... G01N 27/026; G01N 33/383

USPC .......................................................... 324/629
See application file for complete search history.

(56) References Cited

U.S. PATENT DOCUMENTS

| | | | |
|---|---|---|---|
| 5,792,337 A * | 8/1998 | Padovani | G01N 17/02 324/700 |
| 5,900,736 A | 5/1999 | Sovik et al. | |
| 6,400,161 B1 | 6/2002 | Geisel | |
| 6,414,497 B1 | 7/2002 | Sovik et al. | |
| 7,088,115 B1 * | 8/2006 | Glenn | G01N 33/383 324/718 |
| 7,219,024 B2 | 5/2007 | Gamache et al. | |
| 7,289,916 B2 | 10/2007 | Drnevich et al. | |
| 2007/0163368 A1 * | 7/2007 | Yuki | G01N 33/383 73/866 |
| 2009/0170756 A1 | 7/2009 | Burnett, Jr. et al. | |
| 2010/0039125 A1 | 2/2010 | Buchler | |
| 2012/0012470 A1 * | 1/2012 | Bartholomew | G01N 33/383 205/726 |
| 2012/0013354 A1 | 1/2012 | Bowler et al. | |

(Continued)

*Primary Examiner* — Melissa Koval
*Assistant Examiner* — Rahul Maini
(74) *Attorney, Agent, or Firm* — Hoffman Warnick LLC

(57) ABSTRACT

Methods of extracting complex impedance from selected subsurface volumes of a material under test (MUT) using various embodiments of electrode sensor pairs are provided. The electrode pairs can penetrate into a subsurface of the MUT, and operate below the surface of the MUT. Configurations of electrode pair sensors provide measured data of complex impedance of selected subsurface volumes of the MUT using electromagnetic spectrographic signals over a frequency range. The complex impedance characteristics of the subsurface volumes may be used to identify variations in the properties of the MUT, or be correlated to physical properties of the MUT.

20 Claims, 10 Drawing Sheets

(56) References Cited

U.S. PATENT DOCUMENTS

2012/0130212 A1 5/2012 Pluta et al.
2015/0212026 A1 7/2015 Pluta et al.

* cited by examiner

CHARACTERIZATION OF MATERIAL UNDER TEST (MUT) WITH ELECTROMAGNETIC IMPEDANCE SPECTROSCOPY

CROSS-REFERENCE TO RELATED APPLICATION

This application claims priority to U.S. Provisional Application No. 69/039,204, filed on Aug. 19, 2014, which is hereby incorporated by reference in its entirety.

TECHNICAL FIELD

Various embodiments of the invention relates to securing impedance spectrographic characterizations of a material under test, and the design of apparatuses having various conducting electrode configurations for use with electromagnetic impedance spectrographic measurement devices to secure the data for the application of the disclosed method, along with those particular apparatuses. The design of the conducting electrode configurations is applicable to any material that can be penetrated by the electrodes. While the primary example of the disclosure is wet concrete, the approach is also applicable to other materials such as tobacco, grains, wood chips, and saw dust.

BACKGROUND

The majority of transportation infrastructure, e.g., in the United States, including bridges, pavements and runways, tunnels, ports and harbor structures, and parking structures, has ordinary Portland cement (OPC) concrete as its major structural component. High-rise buildings, industrial structures, energy structures (e.g., nuclear power plants, dams, and wind mill foundations) also use significant amounts of concrete, which is the second most used material by humans in terms of volume, after water. The advances in materials science and the technology of OPC concrete over the past few years have brought in revolutionary changes in design and construction.

The advent of high-performance and self-consolidating concretes containing several mineral/chemical admixtures has improved the fresh and hardened concrete properties. However, several areas of concern still exist, especially with respect to adequate characterization of the material (e.g., concrete) for quality control/quality assurance and acceptance criteria when delivered. In addition, novel concretes, such as pervious and roller-compacted concretes are increasingly being used for specific applications. Currently, there exist no quantitative field measurement method to characterize the material prior to its placement to certify the acceptance criteria specified by the designer and its performance prediction. Quality control of concrete in the fresh state is still being ascertained using the slump test (according to American Society for Testing and Materials (ASTM) C143), which is a subjective qualitative test and does not provide a reliable quantification of the state of the material.

SUMMARY

Aspects of the invention include methods, apparatus, and systems to secure electromagnetic impedance characteristics of selected volumes of materials under test (MUT).

Embodiments include systems, apparatuses and related methods. In various embodiments, the systems can include an apparatus having various electrode sensor arrays configured to communicate with various materials under test (MUT). The system(s) can include: a signal generator operably connected with the array of electrodes, the signal generator for transmitting oscillating electromagnetic field signals through the array of electrodes at a range of selected frequencies; a signal detector operably connected to the array of electrodes, the array of electrodes in communication with the material under test; a signal comparator operably connected to the signal generator and the signal detector; and at least one computing device operably connected with the signal comparator. The at least one computing device is configured to determine the electromagnetic impedance characteristics of selected volumes of the MUT. The at least one computing device may also be configured to correlate the electromagnetic impedance characteristics of selected volumes of the MUT to physical properties of those volumes. The at least one computing device may also provide output to a user in various formats, and/or transfer data files to another computer by various means.

The methods, systems and various embodiments of the electrode sensor arrays presented in this disclosure provide improvements over conventional approaches by securing electromagnetic impedance spectrographic characteristic of the MUT which may then correlate the impedance characteristics to physical properties of the MUT.

According to various embodiments shown and described herein, electromagnetic impedance spectrographic characteristics of the MUT can be obtained by forming electrically non-conductive or electrically conductive communication (contact) between an electrode sensor array placed proximate the MUT.

As noted herein, some embodiments described herein can include systems, apparatuses and/or methods configured to determine characteristics of concrete, e.g., fresh concrete. However, it is understood that various embodiments are configured to determine characteristics of a variety of distinct materials other than concrete. As noted above, OPC concrete is a prevalent material in the construction of numerous types of structures. Various embodiments described herein can overcome the current lack of quantitative methods for the adequate characterization of material (e.g., concrete) for quality control/quality assurance, and acceptance criteria. In addition, the approaches described herein also apply to other concretes such as pervious (porous) and/or compacted concretes, which are increasingly being used for specific applications, to assure that the material meets the acceptance criteria specified by the designer and its performance prediction. Further, the methods described may be applied to other materials into which electrodes may be inserted, either destructively or non-destructively, such as grains, wood chips, tobacco bales, slurries and other such materials.

The ultimate condition of the concrete can be highly dependent on its state at the time of delivery as reflected by the amount of free water and the degree of hydration. Accurate and quantitative descriptions of these concrete properties in the fresh state can be critical to strategize decisions related to opening a structure to service, condition assessment, prescribing the extent of repair or the repair schedule, and predicting structural service-life. The ability to provide these and other information of concrete and other MUTs is one objective of the various embodiments presented herein.

A first aspect includes a method of characterizing select volumes of a material under test (MUT) using electromagnetic impedance spectroscopy. The method can include: measuring the complex impedance of volumes of the MUT with an electrode array in electrically conducting or non-conducting communication with the MUT; and applying correlation algorithms to relate the measured complex impedance of one of the volumes of the MUT to physical properties of interest in the MUT. In the case of fresh concrete, the physical properties of interest can include the amount of free water and/or the amount of water that has been hydrated, which is the chemical reaction where the free water combines with the anhydrous cement. For special purposed concretes, such as pervious concrete, the degree of porosity may also be characterized.

A second aspect includes a system including: a set of electrodes for communicating with a subsurface below a surface of a MUT; a signal generator operably connected with the set of electrodes; and at least one computing device operably connected with the signal generator and the set of electrodes, the at least one computing device configured to: instruct the signal generator to transmit electromagnetic signals over a range of frequencies from the set of electrodes to the subsurface; obtain a set of return electromagnetic signals from the set of electrodes after the transmitting of the electromagnetic signals; and determine a characteristic of at least a portion of the subsurface of the MUT based upon the set of return electromagnetic signals (e.g., combining the set of return electromagnetic signals).

A third aspect includes a method of characterizing select volumes within the subsurface of an MUT using a plurality of electrode pairs, the method including: instructing a signal generator to transmit electromagnetic signals over a range of frequencies from the plurality of electrode pairs through the subsurface of the MUT; obtaining a set of return signals from the plurality of electrode pairs after the transmitting of the electromagnetic signals; and determining a characteristic of the subsurface of the MUT based upon the set of return signals (e.g., combining the set of return signals).

A fourth aspect includes a computer program product having program code stored on a computer readable storage medium, which when executed by at least one computing device coupled to a signal generator and a set of electrodes, causes the at least one computing device to execute a method of characterizing a select volume of a MUT by performing actions including: instructing the signal generator to transmit electromagnetic signals over a range of frequencies from the set of electrodes through the select volume of the MUT; obtaining a set of return signals from the set of electrodes after the transmitting of the electromagnetic signals; and determining a characteristic of a select volume of the MUT based upon the return signals (e.g., combining the set of return signals).

A fifth aspect includes a method of characterizing select volumes of a material under test (MUT) using at least one electrode pair, the method including: inserting the at least one electrode pair through a surface of the MUT to reach a subsurface volume of the MUT; instructing a signal generator to transmit a set of spectrographic signals from a transmitting electrode in the at least one electrode pair, through the subsurface volume of the MUT; obtaining a return set of spectrographic signals from the at least one electrode pair after the transmitting of the set of spectrographic signals; and determining, from the return spectrographic signal, a physical characteristic of the subsurface volume of the MUT.

DETAILED DESCRIPTION

The following description expands on and improves the methodology disclosed in conventional approaches to convert the measured impedance in volumes of a material under test (MUT) into physical properties of interest. According to various embodiments, a MUT can include any material capable of being characterized via one or more approaches shown and/or described herein. In various embodiments, a MUT includes any material into which the electrode array (e.g., one or more electrodes) may be inserted either destructively or non-destructively. One aspect of the disclosure focuses on material(s) into which the electrode array may penetrate into the MUT in a non-destructive manner. These materials can include powders, liquids and slurries, e.g., concrete. In various embodiments, an MUT may include an organic material such as a soil, or a biological material such as fluids, etc. An MUT can include synthetic, composite and/or other blended/modified materials. An MUT can also include elemental materials, as well as materials including impurities. It is understood that the teachings described according to the various embodiments herein can be applied to any MUT described herein, as well as other materials that can be characterized according to the approaches of the various embodiments.

As noted herein, various embodiments are directed to methods of quantitative characterization of concrete properties in the fresh state and other materials into which the electrodes may be inserted.

Figure 1:
FIG. 1 is an illustration of forms used to obtain concrete cylinders and the concrete cylinders used to ascertain the strength of concrete.
Figure 1:
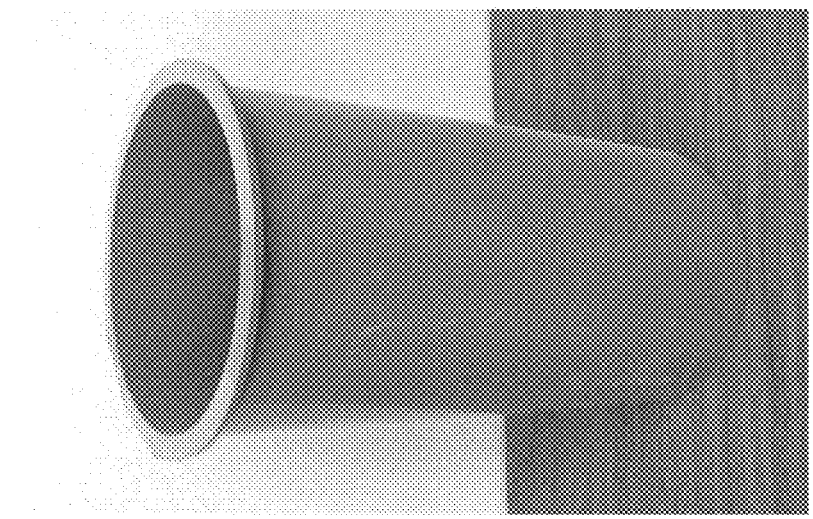

The issue of providing a quantitative means for testing the quality of concrete as it is delivered to a construction site may be important because of the extensive roll concrete plays in all types of infrastructure. The current method of testing for the strength of concrete is based upon ASTM Standards C31 and C39. Typically, out of five truck loads averaging 10 cubic yards of concrete (a total of 1,350 cubic feet), five samples in 6-inch by 12-inch cylinders (a total of 0.65 cubic feet), as shown in FIG. 1a, are taken from one truck. Only one out of five deliveries is sampled, and less than 0.05% of the delivered material supplied is sampled. These cylinders are cured (see FIG. 1b) for 3, 7, 14, and 28 days (respectively) before being placed into a compression tester to see if the strength specifications are met. This sampling approach may lead to problems, e.g., only one in five deliveries are inspected, and that as much as 28 days from the pouring of the concrete passes before a definitive test result is obtained.

The objective of various methods presented herein is to provide a means to quantitatively define the quality of each delivery of concrete as it is delivered. These methods are also applicable to other materials into which the electrodes may be inserted, either destructively or non-destructively.

The use of electromagnetic tomographic and spectrographic measurement devices have been identified in US Patent Application Publication 2013/0307564 and U.S. Provisional Patent Application No. 61/703,488 (each of which is hereby incorporated by reference in its entirety) to locate specified volumes within a material under test and to characterize that volume based upon its electromagnetic characteristics. However, once the basic approaches are disclosed, other applications may be identified and implemented based primarily on changes in the design of the electrode array combined with the previously disclosed art. The ability to change the application or improve on previously disclosed applications also provides the ability to secure data such that the electromagnetic characteristics of specific computational volumes may be readily determined from the electromagnetic properties of measured volumes.

Figure 2:
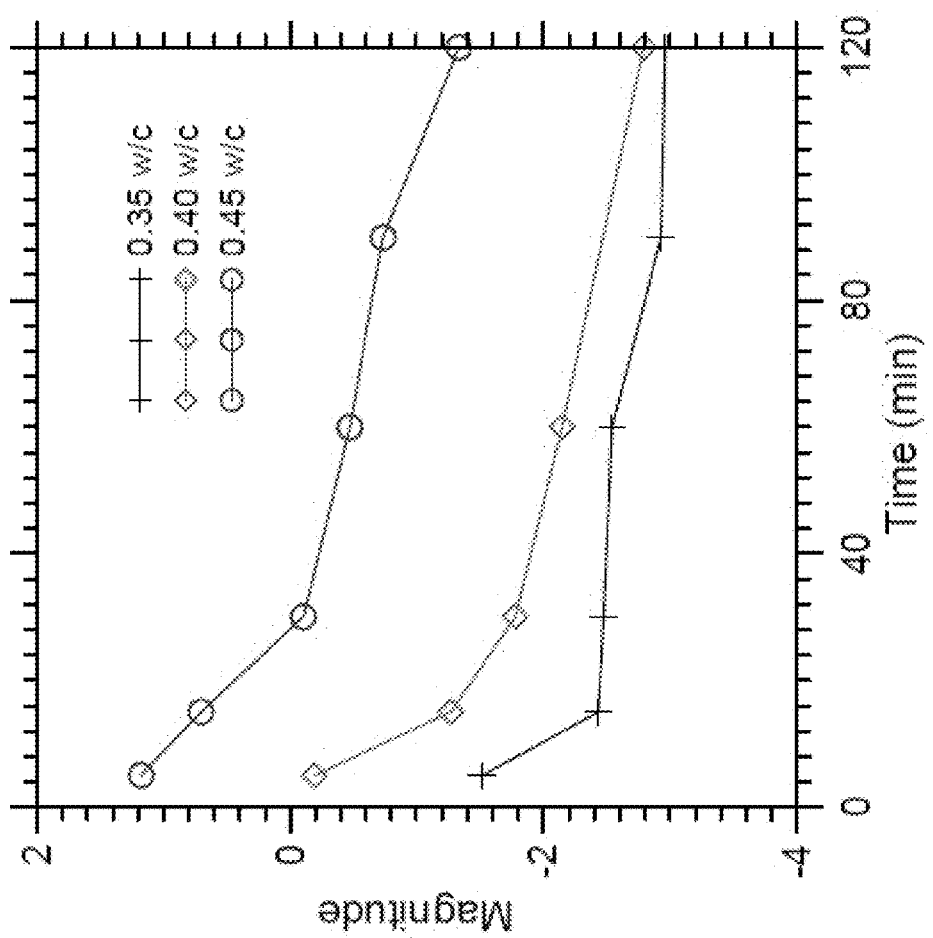
FIG. 2 is a graphical depiction of impedance data over time secured from mixtures of concrete with different water to concrete ratios.

An apparatus including of a sensor array having an electrode allows for securing of data for the computation of electromagnetic characteristic of a volume within the MUT which may then be related to some physical parameter of the MUT. This has been presented in conventional approaches. However, specific to various embodiments described herein, FIG. 2 shows a data representing a measure of the impedance of a MUT, labeled "Magnitude", on the ordinate axis of the plot for similar mixes of concrete with different ratios of the initial mix of water to cement (w/c). The abscissa is the time elapsed from mixing. As can be seen, there is a difference in the measured impedance for the different w/c ratios, which changes as time progress. The reason for the change with respect to time is discussed more fully herein, but FIG. 2 illustrates a specificity in the measured impedance that suggests impedance spectroscopy may be used to characterize the w/c ratio of concrete.

In order to apply the method to secure the impedance data of a measured volume, the inventors have implemented various designs and measuring strategies to obtain accurate data and secure that data in an efficient and timely manner. The methods, systems and apparatuses used by the inventors are the subject of the disclosure herein.

In the following description, reference is made to the accompanying drawings that form a part thereof, and in which is shown by way of illustration specific exemplary embodiments in which the present teachings may be practiced. These embodiments are described in sufficient detail to enable those skilled in the art to practice the present teachings and it is to be understood that other embodiments may be utilized and that changes may be made without departing from the scope of the present teachings. The following description is, therefore, merely exemplary.

Illustrations with respect to one or more implementations, alterations and/or modifications can be made to the illustrated examples without departing from the spirit and scope of the appended claims. In addition, while a particular feature may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of embodiments are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g., −1, −2, −3, −10, −20, −30, etc.

Prior art exists that applies electromagnetic impedance to characterize the properties of various materials using electrodes placed on the surface of an MUT. U.S. Pat. Nos. 5,900,736; 6,400,161; 6,414,497; and 6,677,763 (each of which is hereby incorporated by reference in its entirety) present a two-electrode sensor array as a means to evaluate the density of asphalt using electromagnetic impedance characteristics of the asphalt. These conventional approaches do not use any spectrographic or tomographic approaches, but illustrate two-electrode geometries for use with electromagnetic impedance measuring devices. U.S. Pat. No. 7,219,021 (hereby incorporated by reference in its entirety) presents the use of electromagnetic impedance spectroscopy to evaluate the density and moisture of soils with an electrode geometry similar to that in U.S. Pat. Nos. 5,900,736 and 6,414,497. These electrode arrays are in non-conductive communication with the MUT. US Patent Publication 2013/0307564 and U.S. Provisional Patent Application No. 61/703,488 (each of which is hereby incorporated by reference in its entirety) present two different methods of evaluating a MUT with impedance spectroscopy and impedance tomography with linear electrode arrays in conductive or non-conductive communication with the MUT. U.S. Provisional Patent Application No. 61/906,664 (which is hereby incorporated by reference in its entirety), presents alternate configurations for obtaining electromagnetic tomographic and spectrographic impedance measurements from the surface of the MUT, and converting those measurements into physical parameters.

However, these conventional approaches require that surface of the MUT is solid and dry enough to support the electrode array, or that the electrode array may be positioned at a controlled height above the surface of the MUT. One issue with materials that are wet, such as wet concrete or wet soils, is that anything in direct contact with the surface can result in water being wicked out of the material to form a layer of free water at the surface. Regardless, if the electrode array is in non-conducting or conducting contact, a layer of free water between the electrode array and the MUT could short out the electromagnetic wave field, reducing the chance of obtaining meaningful information about the MUT.

The method and the various embodiments of the electrode sensor arrays presented according to the disclosure provide various improvements over the prior art, particularly where the MUT is not a solid and/or dry material, or located in a position in which the spacing between the electrode array and the MUT may not be controlled. The current disclosure presents methods, systems and computer programs to secure electromagnetic impedance spectrographic characteristics of selected volumes of the MUT, which may then correlate the impedance characteristics to physical properties of the selected volumes of the MUT.

Figure 3:
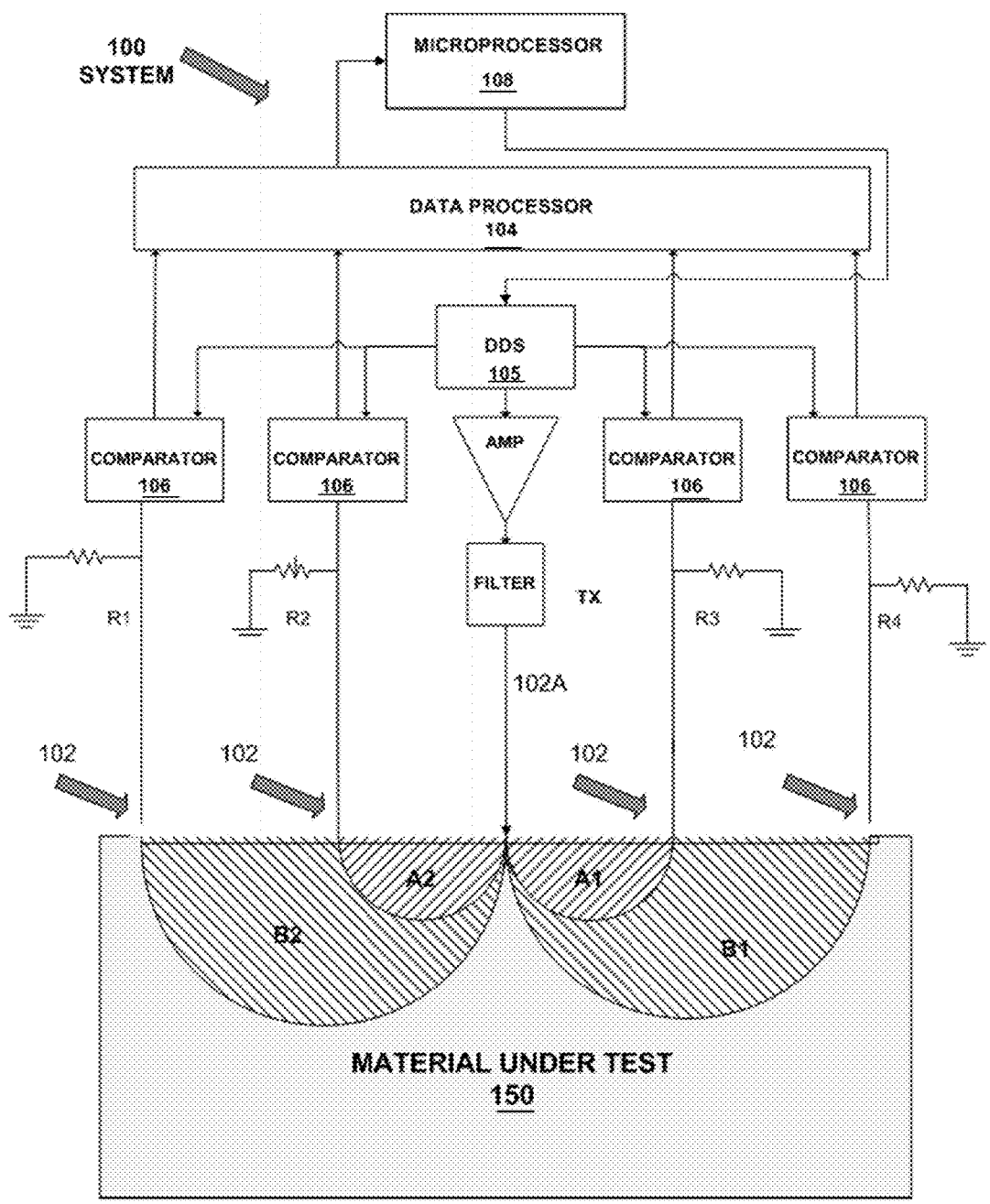
FIG. 3 is a schematic illustration of a five-electrode linear array with variable functions and showing the measured volumes of a material under test (MUT) as described in U.S. Provisional Patent Application No. 61/703,488, which is hereby incorporated by reference in its entirety.

As described in U.S. Provisional Patent Application No. 61/703,488, a schematic depiction of an impedance measuring system is shown in FIG. 3. This schematic depiction shows an impedance sensor system 100 with five electrodes 102, one of which, 102A, provides the input of the signal over a range of frequencies supplied by a signal generator 105, e.g., a DDS (Direct Digital Synthesizer). In this example, the other four electrodes can complete the circuit with the signal passing through the MUT 150. The original signal from the signal generator 104 (DDS) can be compared to the signals passing through MUT 150. The output of the comparator 106 is the difference in the magnitude and the phase shift from the original signal to the return signal. This magnitude and phase data of the transmitted and the return signals can be communicated to microprocessor 108, which processes the data and may transmit it to a user interface or other computer means. The microprocessor 108 can also control DDS 105 to select the frequencies to be generated. In the embodiment shown, the order of the transmitting electrode and the receiving electrodes are fixed.

In this example shown in FIG. 3, electrodes 102 are configured to communicate with the MUT 150, but are not in electrical contact with the MUT 150. That is, the electrodes 102 are electrically isolated from the MUT 150 (e.g., by an insulating material or an air gap). In some cases, the minimum number of electrodes in the array is two (2): a transmitting electrode and a receiving electrode. However, in other applications, the array may consist of a one or two dimensional array of multiple electrodes, e.g., 5 or more electrodes, with the electrodes operating in pairs.

In this example of the prior art, the objective is to characterize the different volumes using a combination of electromagnetic impedance tomography and spectroscopy from the surface of the MUT 150. In contrast, as described herein, various embodiments herein use only electromagnetic impedance spectroscopy, with electrodes in electrical or non-electrical contact with the MUT 150, and located below the surface of the MUT 150.

Figure 4:
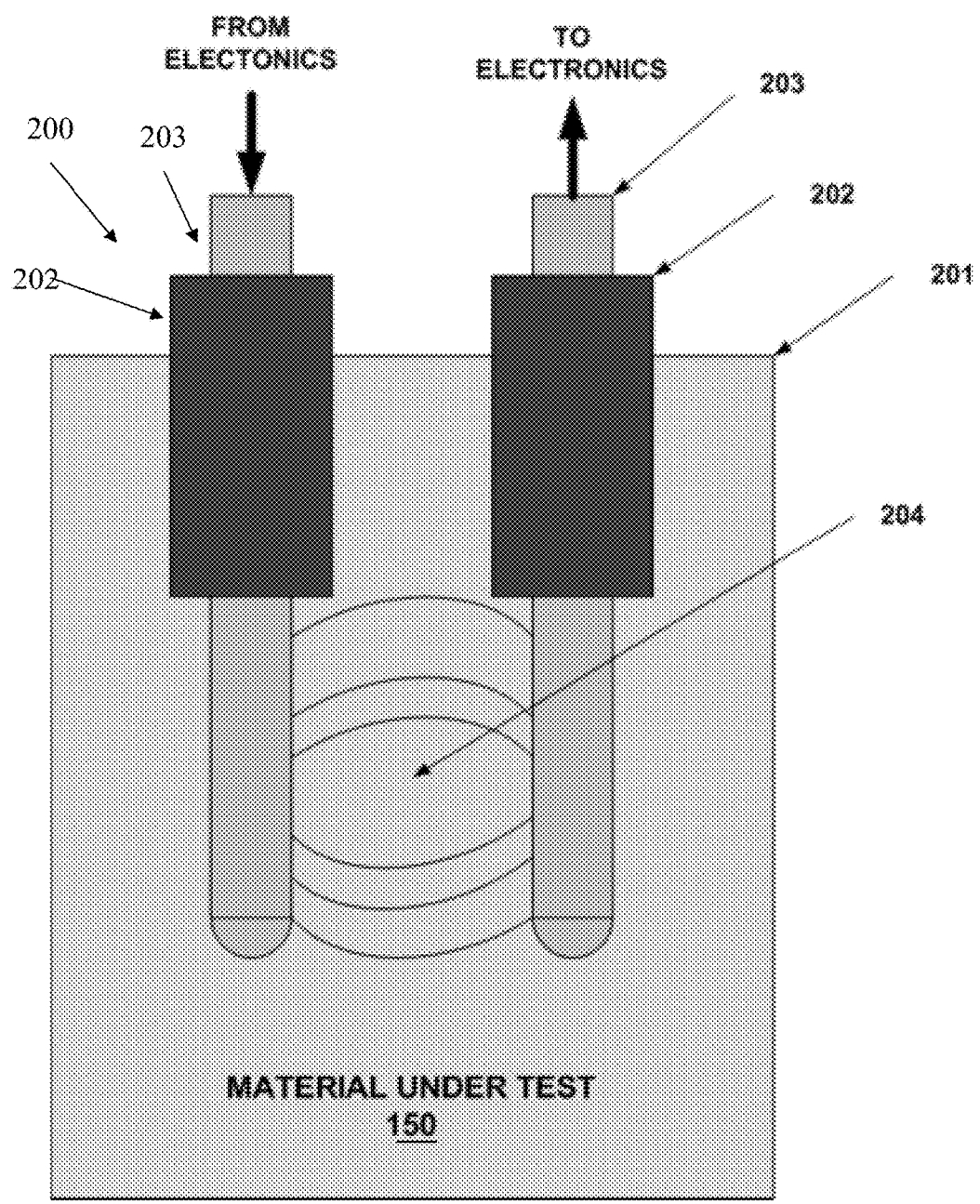
FIG. 4 is a schematic two-dimensional illustration of a conductive two electrode sensor array inserted into a MUT, according to various embodiments.

According to various embodiments, electrodes are inserted into the MUT 150 in order to determine characteristics of that MUT 150. This insertion of the electrodes may result in destructive penetration into the MUT 150 but, in the case of wet or fresh concrete and similar materials, there is nominal permanent deformation of the MUT 150 at best. Referring to FIG. 4, an electrode arrangement 200 is schematically illustrated. In various embodiments, electrode arrangement 200 can be sized for use in the conventional concrete core plastic sample container, such that the spacing of the electrodes (203) as well as their length, is constrained by the physical size of the conventional container (6-inches (15.24-mm) internal diameter and 12-inch (30.48-mm) depth). In some embodiments, the arrangement 200 can include two electrodes 203 which penetrate into the MUT 150 (below its surface) and provide a conductive (electrically conductive) contact with the MUT 150. This may be a beneficial configuration for materials like wet concrete, which contains free water, where conductive electrodes would provide better resistivity data. The free or liquid water permits the flow of ions between the electrodes 203. For other MUTs, like grains, non-conductive (electrically non-conductive) electrodes could be used. Regardless of the type of MUT 150, each of the electrodes is insulated by insulators 202 from the MUT 150 for a portion of their length near to surface 201 and do not transmit or receive electromagnetic signals proximate the surface 201. In various particular embodiments, the length of the insulator (e.g., insulating sleeve) 202, spans between approximately 1-inch (~25-mm) above the surface 201 of the MUT 150 (e.g., concrete) and 1-inch (~25-mm) below the surface 201. As the electrode array 200 may be configured to operate within the conventional sample container, the width of the electrode array 200 may be as small as 4.5-inches (~11-mm) and have a total length of approximately 11-inches (28-mm) from the top of the mold. In various embodiments, the electrical path along the surface 201 of the MUT 150 provides the best electrical path between the two electrodes 203, and will result in the electromagnetic signal travelling along the surface 201 of the MUT 150 rather than through the MUT 150. With the insulators 202 in place and the electromagnetic field not being transmitted along the surface 201, the electromagnetic field will travel through the volume of the MUT 150 as indicated by field lines 204. The electromagnetic characteristics of the MUT 150 can then be measured according to the approaches described herein.

Figure 5:
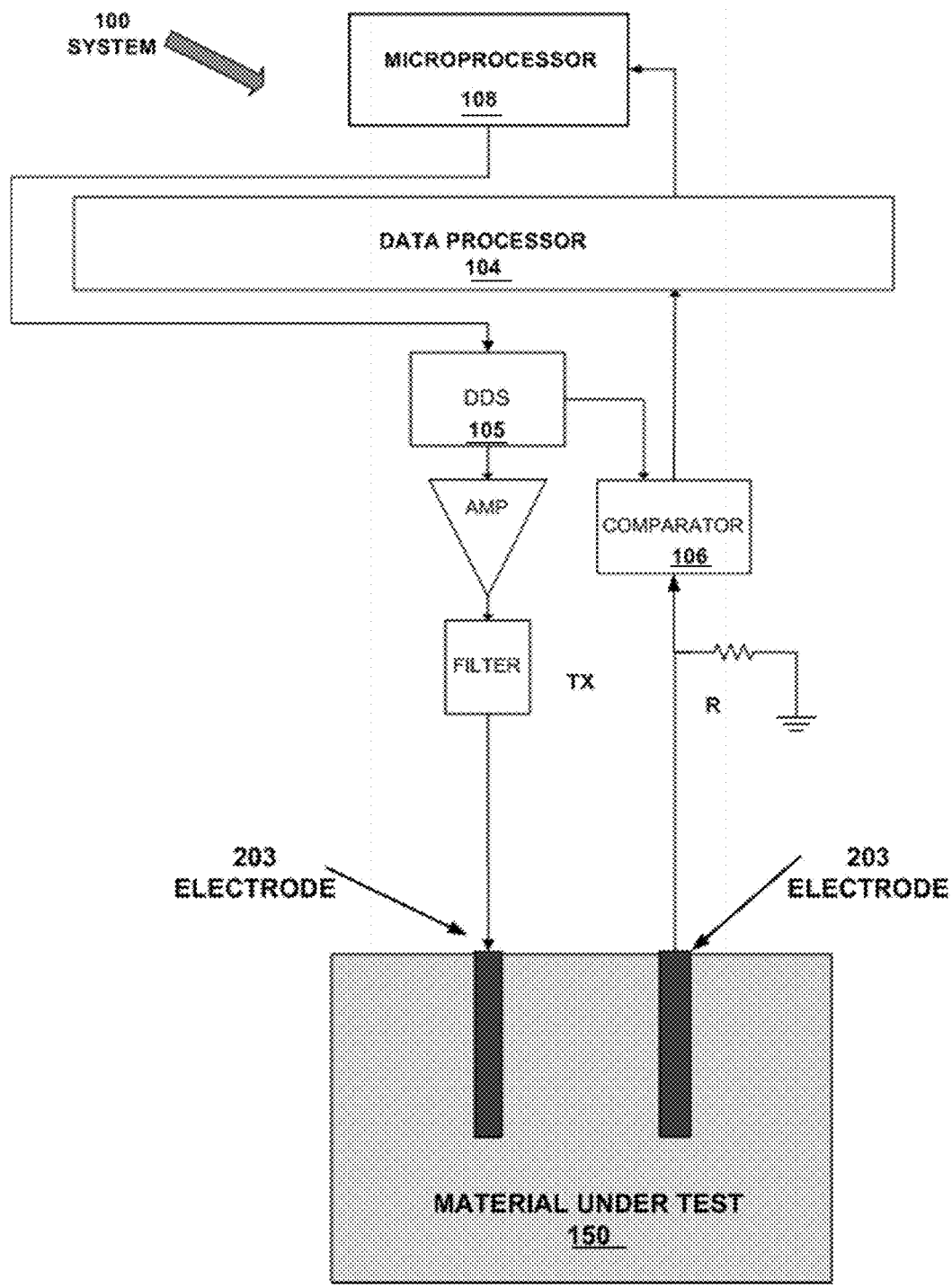
FIG. 5 is a schematic two-dimensional illustration of a conductive two electrode sensor array with electronics, according to various embodiments.

FIG. 5 illustrates the electronics integrated within electrodes 203 to provide the electromagnetic signal to the MUT 150, and how the resultant complex impedance measurements are made. The overall electronic approach according to various embodiments is similar to that shown in FIG. 3, except there is only one electrode pair. The functionality of the DDS 105, comparator 106 and microprocessor 108 are substantially similar to that shown in the system of FIG. 3. The electronics here are shown as an example as to how the functionality of providing an electromagnetic signal, and measuring the impedance, can be accomplished. Among alternate methods of determining impedance in conjunction with the system 100, one is presented in Provisional Patent Application No. 61/787,484 (incorporated herein in its entirety).

In the discussion of the measurements and interpreting aspects of the complex impedance, it may be beneficial to define terms that may be calculated from the output of an electromagnetic measurement device which are the magnitude of the power difference between the transmitted signal and the signal that is transmitted through the MUT, m, and the phase angle, φ, shift between the transmitted signal and the signal transmitted through the MUT. Impedance (Z) is represented mathematically as a complex relation consisting of a real part, resistance, and an imaginary part, reactance:

$$Z=R+iX;$$

$Z$=the complex value of Impedance;

$R=m*\cos \varphi$;the Resistance;

$X=m*\sin \varphi$;the Reactance;

Resistance, R, is a material's opposition to the flow of electric current;

Reactance, X, is a material's opposition to alternating current due to capacitance (capacitive reactance) and/or inductance (inductive reactance);

Admittance (Y) is a complex quantity which is the inverse of Impedance, and results in the definition of the terms of Conductance and Susceptance:

$$Y=1/Z=G+iB;$$

Susceptance (B) is a complementary representation of the reactance in the term admittance and is defined mathematically as:

$$B=-X/(R^2+X^2);$$

The Susceptance may be computed from the measured properties as follows:

$$B = \text{the Susceptance} = -\sin \varphi/m;$$

The Conductance (G) may be computed from the measured properties as follows:

$$G = \text{the Conductance} = \cos \varphi/m.$$

In the description of the various embodiments, the value of the impedance, Z, will be used in the explanations pertaining to the measurements made in an MUT (e.g., MUT 150) and the computation of impedance and MUT physical properties. However, a value of the resistance, reactance, admittance, conductance, or susceptance may replace impedance in any of the examples below.

Figure 6:
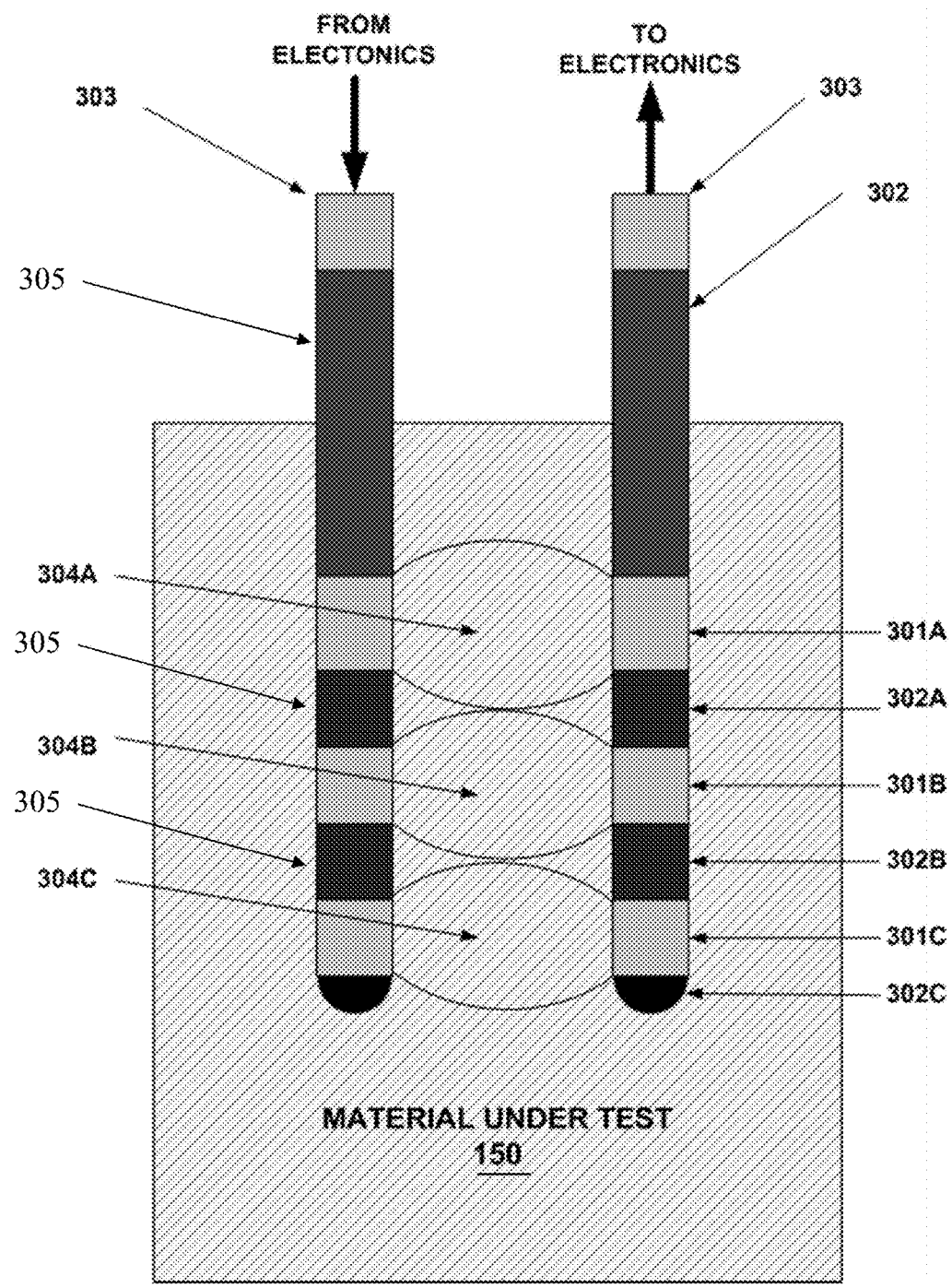
FIG. 6 is a schematic two-dimensional illustration of a segmented conductive two electrode array to measure different volumes of a MUT, according to various embodiments.

In various embodiments, the electrode array 200 shown in FIG. 4 is able to sample the material characteristics of one volume of the MUT 150. According to various embodiments, a segmented electrode 303 as shown in FIG. 6 (two shown) is able to measure the characteristics of various, differentiated volumes of the MUT 150. While there are two electrodes 303 in this configuration (inserted into the MUT 150), there are multiple segments (301A, 301B, and 301C) on the electrodes 303 which may be operated as electrode pairs sequentially, at the same frequency, or simultaneously, at frequencies that vary by some amount. The segments (301A, 301B, 301C) are separated by non-transmitting segments (302A, 302B, and 302C), which may be non-transmitting segments in the electrodes 303, or may be formed by one or more segments of non-conducting sheath 305. The result is that the properties of the volumes 304A, 304B, and 304C in the MUT 150 are measured.

As noted herein with respect to various embodiments, the electrodes may be positioned either in electrical conducting contact or in electrical non-conducting contact with the MUT 150. In various embodiments, the segmented electrodes 303 illustrated in FIG. 6 can be formed using a non-conducting sheath (305) encapsulating the electrodes and there is no electromagnetic signal in the non-conductive areas.

It is also noted that the electrodes 203, 303 in various embodiments must not have any sharp points at their active tips (e.g., for entry into the MUT 150). Whether the end of the electrodes 203, 303 are transmitting, as in FIG. 4, or non-transmitting, as in FIG. 6, the geometry of the end of the electrode may be hemi-spherical.

An alternative embodiment could include more than two electrode probes. Shown in the top-down schematic view in FIG. 7, there are two distinct pairs of electrodes (four total), E1 and E3 and E2 and E4, configured for placement, e.g., in the concrete cylinder form (MUT 150) from FIG. 1a. The spacing between the electrode pairs is one example according to embodiments. However, in some cases, the pairs E1/E3 and E2/E4 are located opposite each other across the center of the cylinder to maximize the volume of the MUT 150 being measured. As described herein, the electrode pairs E1/E3 and E2/E4 may be operated sequentially at the same frequency or simultaneously at frequencies that are slightly varied.

Referring back to FIG. 2, this graph illustrates what the impedance measurement is with various levels of water to cement (w/c), based on weight, with time at one frequency. Cement is substantially composed of anhydrous calcium and silica, $Ca_3SiO_5$. When water is added, there is an exothermic (hydration) reaction, $2Ca_3SiO_5 + 7H_2O \rightarrow 3(CaO).2(SiO_2).4(H_2O)(gel) + 3Ca(OH)_2$, that, along with the aggregate, binders and fillers, results in concrete. The amount of water originally added to the concrete mix is significant to the ultimate strength of the concrete. Initially, all of the water is free. But as time progresses, the water chemically binds with the calcium and silicon in a process called hydration in the exothermic reaction noted above. It can be seen in FIG. 2 that there is a variation in the measured impedance based upon the amount of water originally added, and how long the hydration process has progressed. By the proper selection of frequencies and the component of the complex impedance presented above, the total amount of water and the degree of hydration can be determined. This can provide a quantitative measure of the quality of the concrete as it is delivered.

Figure 7:
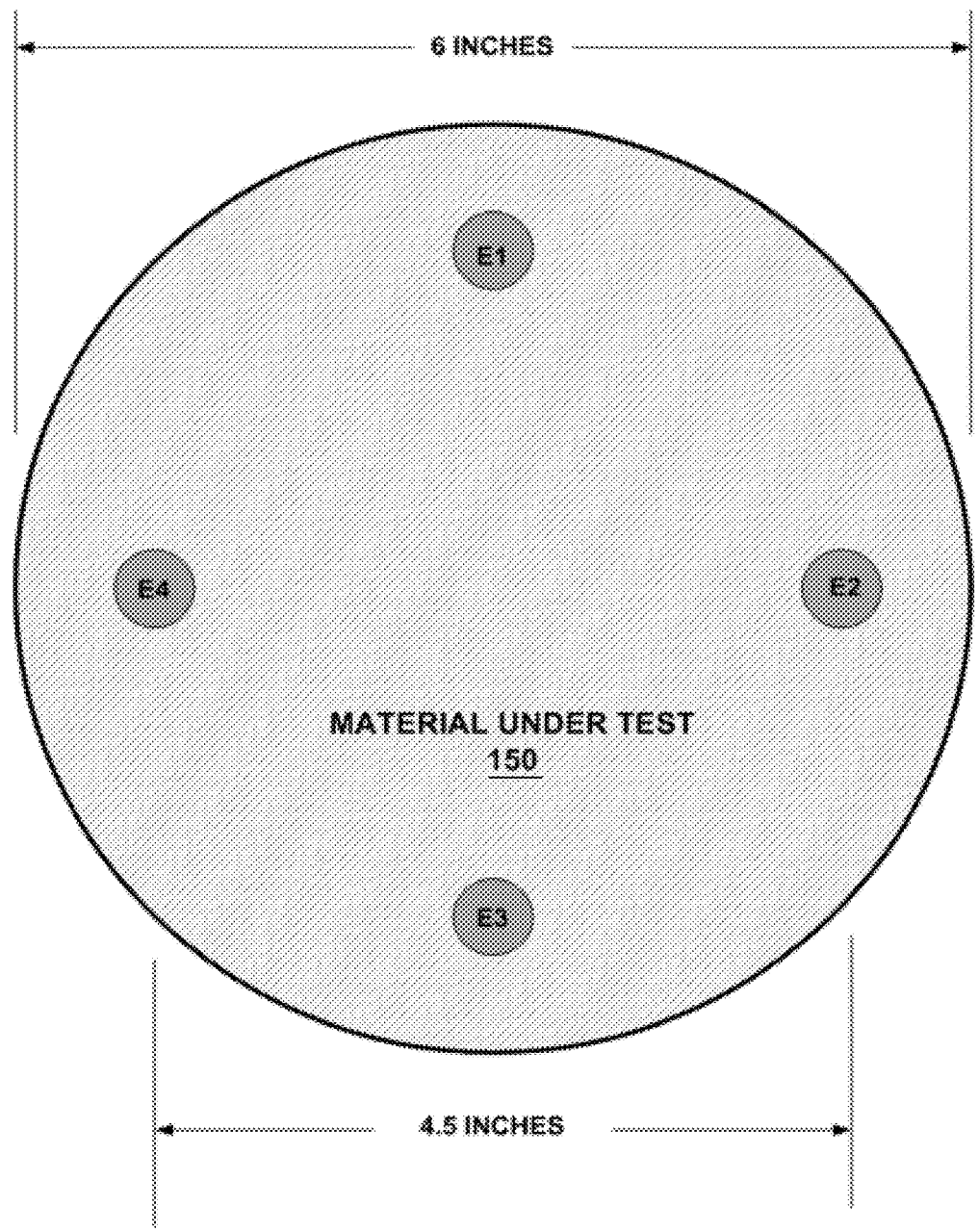
FIG. 7 is a schematic two-dimensional illustration of multiple electrode pairs in a sample of a MUT, according to various embodiments.
Figure 8:
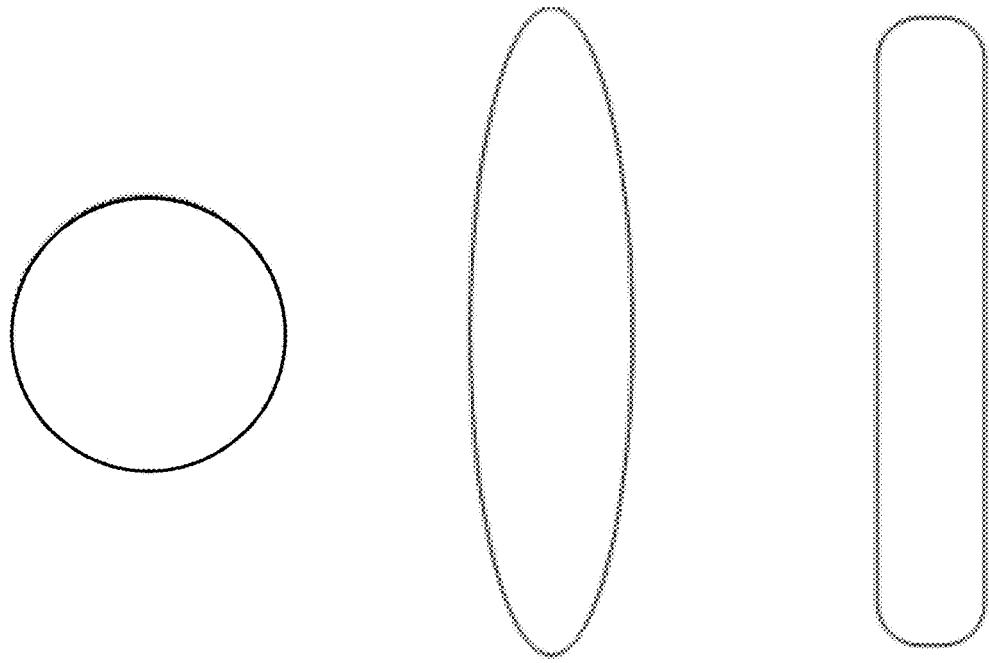
FIG. 8 is schematic illustration showing alternate cross-sectional geometries for penetrating electrodes shown in FIGS. 4-7.

The cross-section shapes of the electrodes used in the illustrations in FIGS. 4-7 may be substantially circular, as shown in FIG. 8a. However, alternate geometries for the electrodes are possible, such as ellipsoid (FIG. 8b), or a rounded rectangle (FIG. 8c). The overriding consideration in the cross-section of an electrode according to various embodiments is that it does not have any points or edges.

Figure 9:
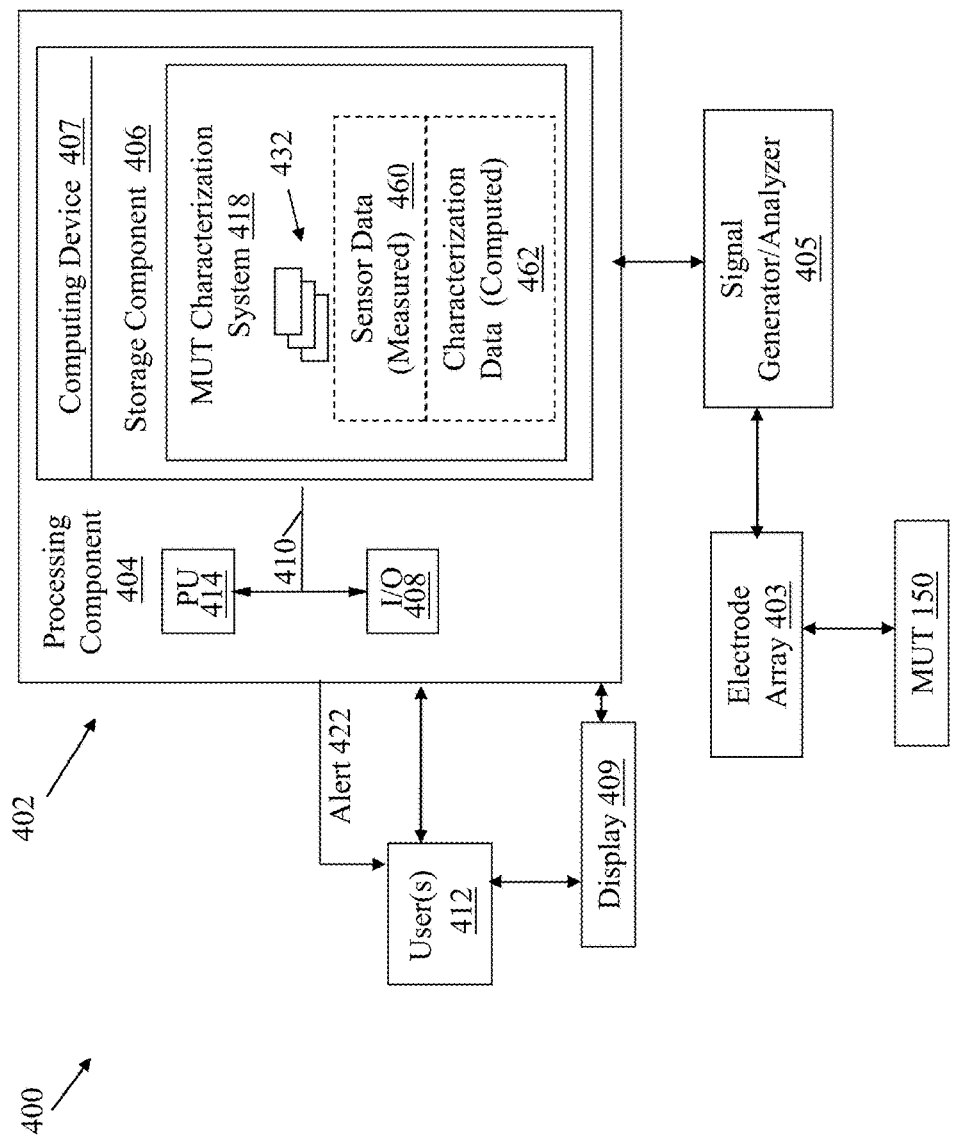
FIG. 9 shows a schematic depiction of a system according to various embodiments.

As described herein, various aspects can include computer implemented methods, systems and computer program products for performing a series of functions. In some cases, as shown in FIG. 9, a system 400 includes an array of electrodes 403 (e.g., electrode pairs 203, 303, E1/E3 and E2/E4, etc.) for communicating (conductively or non-conductively) with a MUT 150 (under a surface of the MUT 150). As described herein, the array of electrodes 403 can be configured in a plurality of distinct ways to detect, and potentially determine the characteristics of selected volumes of an MUT 150. The system 400 can further include a signal generator (in some cases including an analyzer) 405 operably connected (e.g., hard-wired) with the array of electrodes 403. The system 400 can further include at least one computing device 407 operably connected with the signal generator 405 (e.g., wirelessly and/or hard-wired). The at least one computing device 407 is configured to perform various processes.

As used herein, a "voxel" is fraction of a three-dimensional space, that is, a volumetric pixel or volume element that represents a value on a regular grid in three-dimensional space. In some cases, a voxel is known as a three-dimensional equivalent of a pixel (two-dimensional element). Various approaches described allow for determining a physical property of a sub-voxel or a number of sub-voxels of the MUT. In various embodiments, a number of measurements of the physical property(ies) of interest are measured by conventional means and correlated with the measured variations of the measured complex impedance using the arrays/systems/approaches described herein. In various embodiments, the number of measurements can be sufficiently large such that the resulting correlation is statistically significant. The measurements may also be made over a range of frequencies. Further embodiments include a method of developing an algorithm to correlate the physical property to the measured impedance, which may use any number of well known correlation methods such as analysis of variations (ANOVA), neural networks, and multiple regressions. A determination as to which process, impedance characteristic and frequency may ensure that the best fit may be made by selection of the one that provides the most statistically significant results.

Based upon, for example, a known strength and frequency of the transmitted spectrographic signal(s), a configuration of transmitting/receiving electrodes, a strength/frequency of the return spectrographic signal(s), as well as a type of the MUT 150 (e.g., a general composition, known material properties, and/or a depth of penetration), various embodiments include determining characteristics (e.g., density, composition/sub-composition, etc.) of a portion (e.g., volume, sub-volume) of the MUT 150.

For example, referring back to the system 100 of FIG. 5, the transmitting electrode(s) 203 can emit an electromagnetic field over a range of selected frequencies in the MUT 150. The electromagnetic field can be generated by the signal generator (DDS) 105. As described herein, the electrode 203 can be positioned below the surface 201 (FIG. 4) of the MUT 150. The returning electromagnetic field (received at receiving electrode(s) 203) can be compared, using the comparator 106 (and data processor 104), to the transmitted electromagnetic field in the signal generator (DDS) 105 to determine a complex impedance of the material under test 150. That is the data processor 104 and comparator 106 can determine a complex impedance of the material under test 150 based upon a correlation between the difference in the field strength (magnitude) and a phase shift (phase) between the transmitted field and the received field. These values, along with the frequency of the field, can be communicated to the microprocessor 108. The microprocessor controller 104 also controls the DDS 105 to specify the frequencies at which the search or characterization are conducted.

Figure 10:
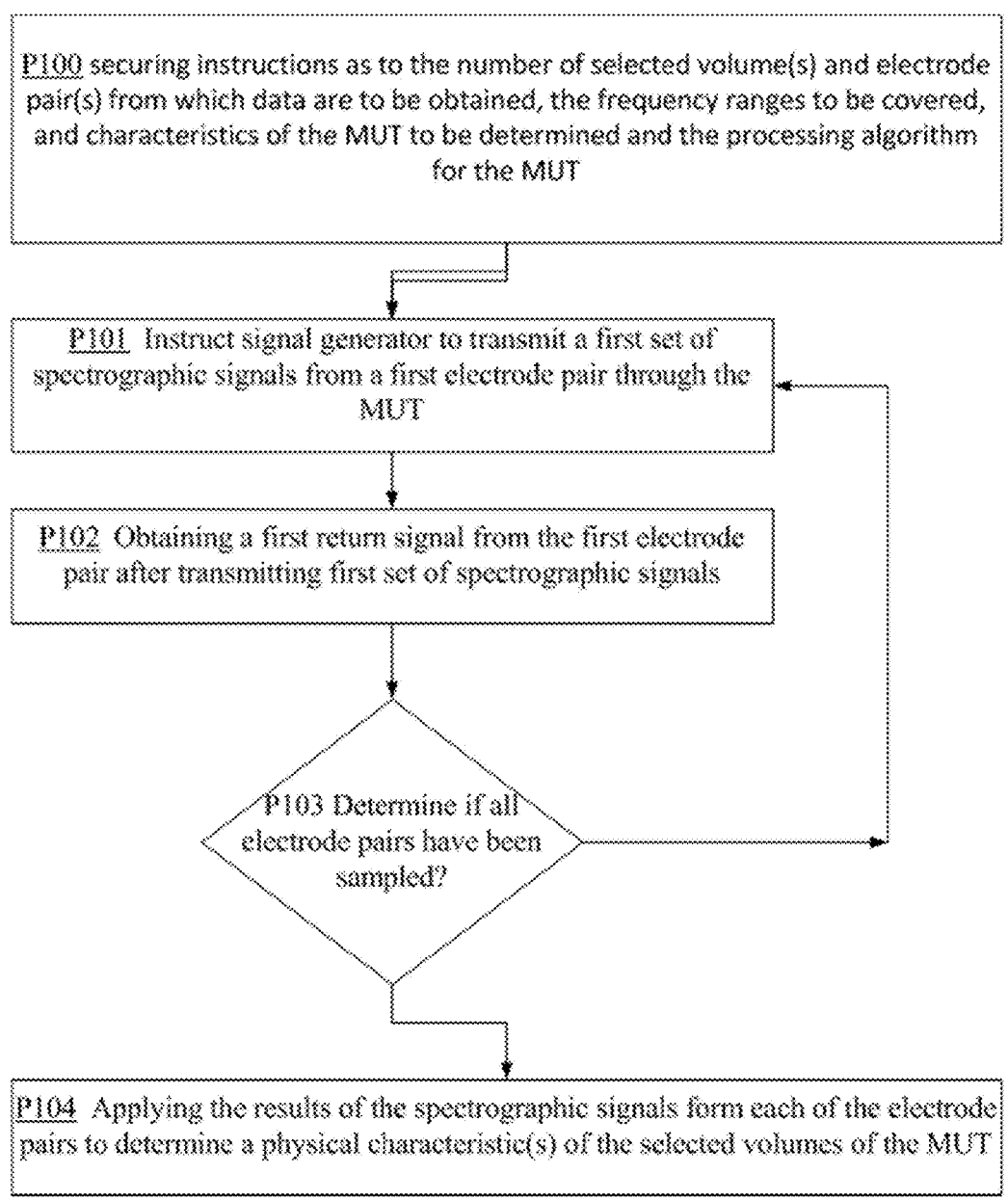
FIG. 10 shows a flow chart illustrating processes performed according to various embodiments.

FIG. 10 shows a flow diagram depicting a method according to various embodiments of the disclosure. The method can be used to characterize one or more select volumes of an MUT using an array of electrodes, as described herein. As shown, the method can include processes including:

Process P100: securing instructions as to the number of selected volumes and electrode pairs from which data are to be obtained, the frequency ranges to be covered, and characteristics of the MUT 150 to be determined and the processing algorithm for the MUT 150, based upon a type of the MUT 150.

P101: instructing a signal generator 405 (e.g., substantially similar to DDS 105) to transmit spectrographic signals over the selected frequency range to the electrode array 403 (e.g., electrodes 203 or electrodes 303) and through the MUT 150;

Process P102: obtaining the return spectrographic signal from the electrode array 403 (e.g., first electrode in either pair 203 or 303);

Process P103: checking to determine if the electrode sampling is complete, and if not, repeating P101 and P102 for any remaining electrode pairs (e.g., pairs E2/E4 shown in FIG. 7). This includes determining whether data has been received from all electrode pairs, in the case of multiple electrode pairs (e.g., FIG. 7); and Process P104: applying the results of the spectrographic signals from each electrode pair(s) to determine a physical characteristic(s) of the selected volume(s) of the MUT 150.

It is understood that process P104 may be performed after P102, in the case that multiple electrode pairs (e.g., E1/E3 and E2/E4) have been sampled. In various embodiments, for example, as shown in FIGS. 4, 5 and 6, only one pair of electrodes (e.g., electrodes 203, 303) is used to sample the MUT 150. In these embodiments, process P3 may include merely verifying that data from the single set of electrodes (e.g., electrodes 203, 303) is obtained.

Returning to FIG. 9, the system 400 for characterizing select volumes of a material under test (MUT) 150 by performing processes described herein with respect to various embodiments is shown in greater detail. To this extent, the system 400 includes a computer system 402 that can perform one or more processes described herein in order to control operation of a sensor array system (e.g., electrode array 403, such as those shown and described with reference to FIGS. 4-6), a signal generator/analyzer 405, and/or a display 409. In particular, the computer system 402 is shown as including an MUT characterization system 418, which makes computer system 402 operable to characterize an MUT by performing any/all of the processes described herein and implementing any/all of the embodiments described herein.

The computer system 402 is shown including the computing device 407, which can include a processing component 404 (e.g., one or more processors), a storage component 406 (e.g., a storage hierarchy), an input/output (I/O) component 408 (e.g., one or more I/O interfaces and/or devices), and a communications pathway 410. In general, the processing component 404 executes program code, such as the MUT characterization system 418, which is at least partially fixed in the storage component 406. While executing program code, the processing component 404 can process data, which can result in reading and/or writing transformed data from/to the storage component 406 and/or the I/O component 408 for further processing. The pathway 410 provides a communications link between each of the components in the computer system 402. The I/O component 408 can comprise one or more human I/O devices, which enable a user (e.g., a human and/or computerized user) 412 to interact with the computer system 402 and/or one or more communications devices to enable the system user 412 to communicate with the computer system 402 using any type of communications link. To this extent, the MUT characterization system 418 can manage a set of interfaces (e.g., graphical user interface(s), application program interface, etc.) that enable human and/or system users 412 to interact with the MUT characterization system 418. Further, the MUT characterization system 418 can manage (e.g., store, retrieve, create, manipulate, organize, present, etc.) data, such as measured sensor data 460 and/or computed characterization data 462 using any solution. It is understood that the sensor data 460 can include data obtained by the electrode array (e.g., pair(s)) 403 about the MUT 150. Computed characterization data 462 can include one or more physical characteristic of the MUT 150. The MUT characterization system 418 can additionally communicate with signal generator/analyzer 403, user 412 and/or display 409, e.g., via wireless and/or hardwired means.

In any event, the computer system 402 can comprise one or more general purpose computing articles of manufacture (e.g., computing devices) capable of executing program code, such as the MUT characterization system 418, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, the MUT characterization system 418 can be embodied as any combination of system software and/or application software. It is further understood that the MUT characterization system 418 can be implemented in a cloud-based computing environment, where one or more processes are performed at distinct computing devices (e.g., a plurality of computing devices 407), where one or more of those distinct computing devices may contain only some of the components shown and described with respect to the computing device 407 of FIG. 9.

Further, the MUT characterization system 418 can be implemented using a set of modules 432. In this case, a module 432 can enable the computer system 402 to perform a set of tasks used by the MUT characterization system 418, and can be separately developed and/or implemented apart from other portions of the MUT characterization system 418. As used herein, the term "component" means any configuration of hardware, with or without software, which implements the functionality described in conjunction therewith using any solution, while the term "module" means program code that enables the computer system 402 to implement the functionality described in conjunction therewith using any solution. When fixed in a storage component 406 of a computer system 402 that includes a processing component 404, a module is a substantial portion of a component that implements the functionality. Regardless, it is understood that two or more components, modules, and/or systems may share some/all of their respective hardware and/or software. Further, it is understood that some of the functionality discussed herein may not be implemented or additional functionality may be included as part of the computer system 402.

When the computer system 402 comprises multiple computing devices, each computing device may have only a portion of MUT characterization system 418 fixed thereon (e.g., one or more modules 432). However, it is understood that the computer system 402 and MUT characterization system 418 are only representative of various possible equivalent computer systems that may perform a process described herein. To this extent, in other embodiments, the functionality provided by the computer system 402 and MUT characterization system 418 can be at least partially implemented by one or more computing devices that include any combination of general and/or specific purpose hardware with or without program code. In each embodiment, the hardware and program code, if included, can be created using standard engineering and programming techniques, respectively.

Regardless, when the computer system 402 includes multiple computing devices, the computing devices can communicate over any type of communications link. Further, while performing a process described herein, the computer system 402 can communicate with one or more other computer systems using any type of communications link. In either case, the communications link can comprise any combination of various types of wired and/or wireless links; comprise any combination of one or more types of networks; and/or utilize any combination of various types of transmission techniques and protocols.

The computer system 402 can obtain or provide data, such as sensor data 460 and/or computed physical characterization data 462 using any solution. The computer system 402 can generate sensor data 460 and/or computed characterization data 462, from one or more data stores, receive sensor data 260 and/or computed characterization data 462, from another system such as the electrode array 403, signal generator/analyzer 405, user 412 and/or display 409, send sensor data 460 and/or computed characterization data 462 to another system, etc.

While shown and described herein as a method and system for characterizing an MUT, it is understood that aspects of the invention further provide various alternative embodiments. For example, in one embodiment, the invention provides a computer program fixed in at least one computer-readable medium, which when executed, enables a computer system to detect and characterize at least a portion of an MUT. To this extent, the computer-readable medium includes program code, such as the MUT characterization system 418 (FIG. 9), which implements some or all of the processes and/or embodiments described herein. It is understood that the term "computer-readable medium" comprises one or more of any type of tangible medium of expression, now known or later developed, from which a copy of the program code can be perceived, reproduced, or otherwise communicated by a computing device. For example, the computer-readable medium can comprise: one or more portable storage articles of manufacture; one or more memory/storage components of a computing device; paper; etc.

In another embodiment, the invention provides a method of providing a copy of program code, such as the MUT characterization system 418 (FIG. 9), which implements some or all of a process described herein. In this case, a computer system can process a copy of program code that implements some or all of a process described herein to generate and transmit, for reception at a second, distinct location, a set of data signals that has one or more of its characteristics set and/or changed in such a manner as to encode a copy of the program code in the set of data signals. Similarly, an embodiment of the invention provides a method of acquiring a copy of program code that implements some or all of a process described herein, which includes a computer system receiving the set of data signals described herein, and translating the set of data signals into a copy of the computer program fixed in at least one computer-readable medium. In either case, the set of data signals can be transmitted/received using any type of communications link.

In still another embodiment, the invention provides a method of generating a system for characterizing an MUT. In this case, a computer system, such as the computer system 402 (FIG. 9), can be obtained (e.g., created, maintained, made available, etc.) and one or more components for performing a process described herein can be obtained (e.g., created, purchased, used, modified, etc.) and deployed to the computer system. To this extent, the deployment can comprise one or more of: (1) installing program code on a computing device; (2) adding one or more computing and/or I/O devices to the computer system; (3) incorporating and/or modifying the computer system to enable it to perform a process described herein; etc.

In any case, the technical effect of the invention, including, e.g., the MUT characterization system 418, is to control operation of an electrode array 403, signal generator/analyzer 405, user 412 and/or display 409 to characterize at least a portion of an MUT 150 in one of the various manners described and illustrated herein.

According to various embodiments described herein, additional methods, systems and computer program products are disclosed to characterize one or more select volumes of a MUT. For example, one method (with reference to FIGS. 4, 6 and 9) of characterizing select volumes of a material under test (MUT) using at least one electrode pair 403 (203, 303) includes:

A) inserting the at least one electrode pair 403 (203, 303) through a surface of the MUT 150 to reach a subsurface volume of the MUT (e.g., 304A, 304B, FIG. 6);

B) instructing a signal generator 405 to transmit a set of spectrographic signals from a transmitting electrode 203, 303 in the at least one electrode pair, through the subsurface volume of the MUT 150;

C) obtaining a return set of spectrographic signals from the at least one electrode pair 403 (200, 303) after the transmitting of the set of spectrographic signals; and D) determining, from the return spectrographic signal, a physical characteristic of the subsurface volume of the MUT (e.g., 304A, 304B, FIG. 6).

In various embodiments, the return spectrographic signal includes complex impedance data about the subsurface volume (e.g., 304A, 304B, FIG. 6), and the complex impedance data is correlated with at least one physical property of the MUT.

In various embodiments, in process (C), the obtaining of the return set of spectrographic signals includes receiving, at a receiving electrode 203, 303 in the at least one electrode pair, the set of spectrographic signals from the transmitting electrode 203, 303 after passing through the subsurface volume of the MUT (e.g., 304A, 304B, FIG. 6).

In various embodiments, as described herein, the at least one electrode pair includes a plurality of electrode pairs.

According to various embodiments, an additional method of characterizing at least one subsurface volume of a material under test (MUT) using electromagnetic impedance spectroscopy is disclosed. This method can include:

i) Measuring a complex impedance about the at least one subsurface volume of the MUT over a range of frequencies with an electrode pair inserted into and in electromagnetic communication with the MUT; and ii) Applying an algorithm to correlate aspects of the measured complex impedance to physical characteristics of the MUT.

In some cases, the electrode pair are in electrically conductive contact with the MUT. In other cases, the electrode pair are in electrically non-conductive contact with the MUT. According to various embodiments, the electrode pair does not transmit an electromagnetic field through an upper surface of the MUT. According to various embodiments, the base of each electrode in the electrode pair is rounded. In some cases, each electrode in the electrode pair has a cross section including one of: a circular cross-section, an elliptical cross-section or a rounded rectangular cross-section. According to various embodiments, the area of each electrode in the electrode pair is substantially uniform along a length of each electrode.

In some cases, the at least one electrode pair includes a plurality of electrode pairs, and each electrode pair is operated over a frequency range sequentially. In other particular cases, where the at least one electrode pair includes a plurality of electrode pairs, each electrode pair can be operated simultaneously over a frequency range, with the frequency of each electrode pair operating at a different frequency than the other electrode pairs at any given time.

In various embodiments, components described as being "coupled" to one another can be joined along one or more interfaces. In some embodiments, these interfaces can include junctions between distinct components, and in other cases, these interfaces can include a solidly and/or integrally formed interconnection. That is, in some cases, components that are "coupled" to one another can be simultaneously formed to define a single continuous member. However, in other embodiments, these coupled components can be formed as separate members and be subsequently joined through known processes (e.g., fastening, ultrasonic welding, bonding).

The terminology used herein is for the purpose of describing particular example embodiments only and is not intended to be limiting. As used herein, the singular forms "a", "an" and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on", "engaged to", "connected to" or "coupled to" another element or layer, it may be directly on, engaged, connected or coupled to the other element or layer, or intervening elements or layers may be present. In contrast, when an element is referred to as being "directly on," "directly engaged to", "directly connected to" or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Spatially relative terms, such as "inner," "outer," "beneath", "below", "lower", "above", "upper" and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A system comprising:
an electrode pair for communicating through a volume beneath a surface, wherein a portion of each electrode in the electrode pair is encapsulated by a non-conducting sheath, wherein the non-conducting sheath is located on each electrode to transect the surface of a material under test (MUT) while the electrode pair penetrates the volume beneath the surface;
a signal generator operably connected with the electrode pair; and
at least one computing device operably connected with the signal generator and the electrode pair, the at least one computing device configured to:
instruct the signal generator to transmit a set of electromagnetic spectrographic signals from a first electrode of the electrode pair through a portion of the volume beneath the surface of the MUT;
obtain a return electromagnetic spectrographic signal from a second electrode of the electrode pair after the transmitting of the set of electromagnetic spectrographic signals through the volume beneath the surface of the MUT;
compute a complex impedance of the volume beneath the surface of the MUT from the return electromagnetic spectrographic signal; and
determine at least one physical characteristic of the volume beneath the surface of the MUT from the computed complex impedance.

2. The system of claim 1, wherein the obtaining of the return signal includes receiving, at the second electrode in the electrode pair, at least one of the set of electromagnetic spectrographic signals from the first electrode after passing through the subsurface volume of the MUT, wherein complex impedance data from the return signal set of spectrographic signals through the volume beneath the surface is correlated with at least one physical property of the volume beneath the surface of the MUT.

3. The system in claim 1, wherein a portion of each electrode in the pair not encapsulated by the non-conducting sheath is configured for electrically conductive contact with the volume beneath the surface of the MUT by transmitting an electromagnetic field through the volume.

4. The system in claim 1, wherein a portion of each electrode in the electrode pair encapsulated by the non-conducting sheath is configured to be inserted beneath the surface and maintain electrically non-conductive contact with the volume beneath the surface of the MUT.

5. The system in claim 1, wherein a base of each of the electrodes in the pair is rounded.

6. The system of claim 1, wherein each of the electrodes in the pair has a base having a cross-section selected from the group consisting of: circular, ellipsoid and rectangular with rounded corners.

7. The system of claim 1, further comprising a plurality of electrode pairs, wherein each electrode pair in the plurality of electrode pairs is operated over a distinct frequency range of electromagnetic spectrographic signals from a frequency range of all of the other electrode pairs in the plurality of electrode pairs, wherein each of the electrode pairs communicates through the surface sequentially, according to the frequency range for that electrode pair.

8. The system of claim 1, further comprising a plurality of electrode pairs, wherein each electrode pair in the plurality of electrode pairs is operated sequentially over the same range of frequencies of the electromagnetic spectrographic signals to secure spectrographic data about different paths through the volume of the MUT beneath the surface.

9. The system of claim 1, wherein the MUT is fresh concrete.

10. The system of claim 9, wherein the at least one physical characteristic of the subsurface volume includes an amount of free water in the fresh concrete or an amount of water that has been hydrated.

11. The system of claim 1, wherein the signal generator is configured to transmit the set of electromagnetic spectrographic signals over a range of frequencies.

12. The system of claim 11, wherein the range of frequencies over which the set of electromagnetic spectrographic signals are transmitted is from 1 kilo-Hertz (kHz) to 50 mega-Hertz (MHz).

13. A computer program product comprising program code stored on a non-transitory computer readable storage medium, which when executed by at least one computing device coupled to a signal generator and a plurality of electrode pairs, causes the at least one computing device to execute a method of characterizing select subsurface volumes of a material under test (MUT) by performing actions including:
instructing the signal generator to transmit a set of electromagnetic spectrographic signals from a transmitting electrode in one of the electrode pairs through a subsurface volume of the MUT; obtaining a set of return electromagnetic spectrographic signals from a receiving electrode in one of the electrode pairs after the transmitting of the set of electromagnetic spectrographic signals;
computing a complex impedance of the subsurface volume of the MUT from the set of return electromagnetic spectrographic signals; and
determining, from the computed complex impedance of the subsurface volume of the MUT, at least one physical characteristic of the subsurface volume of the MUT, wherein a portion of each of the transmitting electrode and the receiving electrode is encapsulated by a non-conducting sheath, wherein the non-conducting sheath is located on each electrode to transect a surface of the MUT while each electrode penetrates the subsurface volume and the signal generator transmits the set of electromagnetic spectrographic signals from one of the electrode pairs through the subsurface volume of the MUT.

14. The computer program product of claim 13, wherein the set of return electromagnetic spectrographic signals includes complex impedance data about the subsurface volume, and wherein the complex impedance data about the subsurface volume is correlated with at least one physical property of the MUT.

15. The computer program product of claim 14, wherein the MUT includes fresh concrete, and wherein at least one physical property of the MUT includes at least one of an amount of free water in the concrete or an amount of water that has been hydrated.

16. A method of characterizing select volumes of a material under test (MUT) using at least one electrode pair, the method comprising:
inserting the at least one electrode pair through a surface of the MUT to reach a subsurface volume of the MUT, wherein a portion of each electrode in the at least one electrode pair is encapsulated by a non-conducting sheath, wherein the non-conducting sheath is located on each electrode to transect the surface of the MUT while the at least one electrode pair penetrates the volume beneath the surface;

instructing a signal generator to transmit a set of electromagnetic spectrographic signals from a transmitting electrode in the at least one electrode pair, through the subsurface volume of the MUT;

obtaining a return set of electromagnetic spectrographic signals from a receiving electrode in the at least one electrode pair after the transmitting of the set of electromagnetic spectrographic signals;

computing a complex impedance of the subsurface volume of the MUT from the set of return electromagnetic spectrographic signals; and determining, from the complex impedance of the subsurface volume of the MUT, at least one physical characteristic of the subsurface volume of the MUT.

17. The method of claim 16, wherein the return electromagnetic spectrographic signal includes complex impedance data about the subsurface volume, wherein the complex impedance data is correlated with at least one physical property of the MUT.

18. The method of claim 17, wherein the obtaining of the return set of electromagnetic spectrographic signals includes receiving, at a receiving electrode in the at least one electrode pair, the set of electromagnetic spectrographic signals from the transmitting electrode after passing through the subsurface volume of the MUT.

19. The method of claim 17, wherein the MUT includes fresh concrete, and wherein at least one physical property of the MUT includes at least one of an amount of free water in the fresh concrete or an amount of water that has been hydrated.

20. The method of claim 16, wherein the at least one electrode pair includes a plurality of electrode pairs.

* * * * *